(12) United States Patent
Filson, II et al.

(10) Patent No.: US 8,541,758 B1
(45) Date of Patent: Sep. 24, 2013

(54) ULTRAVIOLET REACTOR

(75) Inventors: John R. Filson, II, Mechanicsburg, PA (US); Jesse Rodriguez, Denver, NC (US)

(73) Assignee: Aqua Treatment Services, Inc., Mechanicsburg, PA (US)

( * ) Notice: Subject to any disclaimer, the term of this patent is extended or adjusted under 35 U.S.C. 154(b) by 0 days.

(21) Appl. No.: 13/525,968

(22) Filed: Jun. 18, 2012

Related U.S. Application Data

(60) Provisional application No. 61/498,213, filed on Jun. 17, 2011.

(51) Int. Cl.
*C02F 1/32* (2006.01)
*C02F 1/30* (2006.01)
*A61L 2/10* (2006.01)
*A61L 9/20* (2006.01)

(52) U.S. Cl.
CPC . *C02F 1/325* (2013.01); *C02F 1/32* (2013.01); *A61L 9/20* (2013.01)
USPC ................. 250/455.11; 250/453.11

(58) Field of Classification Search
CPC ........ C02F 1/32; C02F 1/325; C02F 2301/02; C02F 2201/328; A61L 9/20; B01J 2219/0877
USPC ...................... 250/453.11, 455.11
See application file for complete search history.

(56) References Cited

U.S. PATENT DOCUMENTS

| | | | | |
|---|---|---|---|---|
| 5,017,835 A | * | 5/1991 | Oechsner | 315/111.81 |
| 5,075,594 A | * | 12/1991 | Schumacher et al. | 315/111.21 |
| 5,352,359 A | * | 10/1994 | Nagai et al. | 210/192 |
| 5,369,336 A | * | 11/1994 | Koinuma et al. | 315/111.21 |
| 5,512,253 A | * | 4/1996 | Woodbridge et al. | 422/186 |
| 5,952,663 A | | 9/1999 | Blatchley, III et al. | |
| 5,973,447 A | * | 10/1999 | Mahoney et al. | 313/359.1 |
| 6,167,112 A | * | 12/2000 | Schneider | 378/43 |
| 6,320,388 B1 | * | 11/2001 | Sun et al. | 324/464 |
| 6,332,981 B1 | * | 12/2001 | Loyd | 210/198.1 |
| 6,500,387 B1 | * | 12/2002 | Bigelow | 422/24 |
| 6,518,567 B1 | * | 2/2003 | Ganeev et al. | 250/282 |
| 6,633,133 B1 | * | 10/2003 | Ishida | 315/111.81 |
| 6,683,313 B2 | * | 1/2004 | Chen et al. | 250/455.11 |
| 6,700,329 B2 | * | 3/2004 | Giapis et al. | 315/111.21 |
| 6,728,337 B2 | * | 4/2004 | McGeoch | 378/119 |
| 7,018,544 B2 | * | 3/2006 | Veenstra et al. | 210/748.11 |
| 7,116,054 B2 | * | 10/2006 | Zhurin | 315/111.41 |
| 7,326,937 B2 | * | 2/2008 | Mehta et al. | 250/423 R |
| 7,400,096 B1 | * | 7/2008 | Foster et al. | 315/111.41 |
| 7,586,109 B2 | * | 9/2009 | Perel et al. | 250/492.21 |
| 7,622,727 B2 | * | 11/2009 | Shirai et al. | 250/504 R |
| 7,691,343 B2 | * | 4/2010 | Ueberall | 422/186.3 |
| 7,692,165 B2 | * | 4/2010 | Winkler | 250/492.21 |
| 7,714,965 B2 | * | 5/2010 | Chien et al. | 349/124 |
| 7,855,357 B2 | * | 12/2010 | Truche et al. | 250/288 |
| 7,862,728 B2 | | 1/2011 | Yencho | |
| RE43,078 E | * | 1/2012 | Cody et al. | 250/288 |
| 8,207,496 B2 | * | 6/2012 | Makarov et al. | 250/288 |
| 8,217,343 B2 | * | 7/2012 | Cooley et al. | 250/288 |

(Continued)

*Primary Examiner* — David A Vanore

(74) *Attorney, Agent, or Firm* — Hooker & Habib, P.C.

(57) ABSTRACT

An ultraviolet reactor for irradiating a flow of fluid includes a set of UV lamps and baffles spaced along the ramps. The baffles generate helical flow of the fluid flowing along the lamps to enhance exposure of microorganisms carried in the fluid to UV radiation.

14 Claims, 4 Drawing Sheets

(56) References Cited

U.S. PATENT DOCUMENTS

| | | | |
|---|---|---|---|
| 8,246,839 B2* | 8/2012 | Ueberall | 210/748.1 |
| 8,293,185 B2* | 10/2012 | Baron | 422/186.3 |
| 8,357,305 B2* | 1/2013 | Theodore et al. | 210/748.16 |
| 2004/0031436 A1* | 2/2004 | Price et al. | 117/2 |
| 2005/0163653 A1* | 7/2005 | Crawford et al. | 422/24 |
| 2005/0279458 A1* | 12/2005 | Okumura et al. | 156/345.47 |
| 2007/0063147 A1* | 3/2007 | Yamazaki et al. | 250/424 |
| 2011/0109226 A1* | 5/2011 | Cooley et al. | 315/111.21 |
| 2011/0175531 A1* | 7/2011 | Urdahl et al. | 315/111.21 |
| 2011/0180699 A1* | 7/2011 | Cooley et al. | 250/282 |
| 2011/0181169 A1* | 7/2011 | Eden et al. | 313/231.31 |
| 2011/0192968 A1* | 8/2011 | Makarov et al. | 250/282 |
| 2012/0063966 A1* | 3/2012 | Liao et al. | 422/186 |
| 2012/0192792 A1* | 8/2012 | Mahajani et al. | 118/723 R |
| 2012/0235056 A1* | 9/2012 | Makarov et al. | 250/423 R |

* cited by examiner

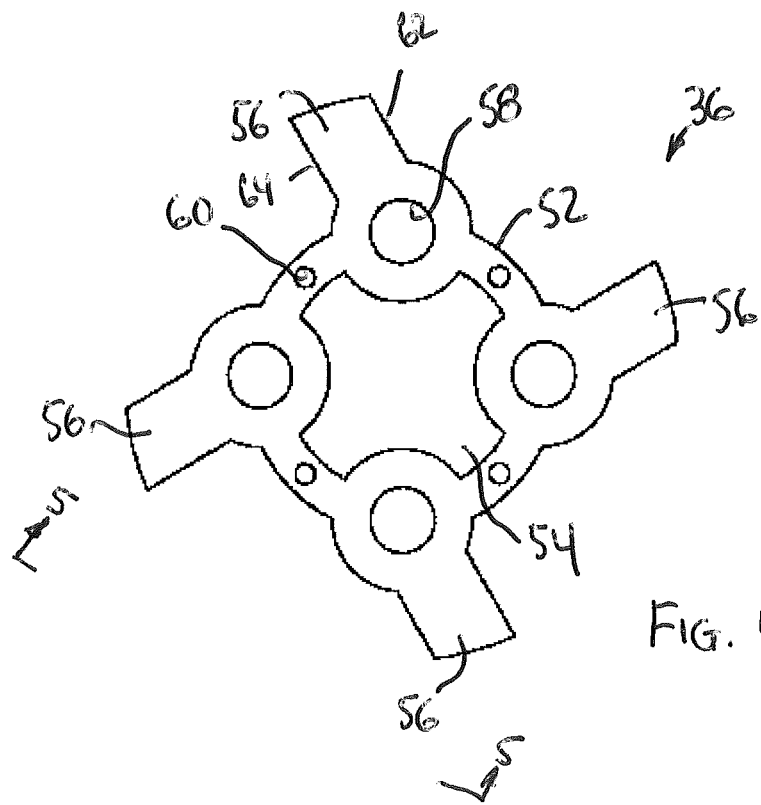
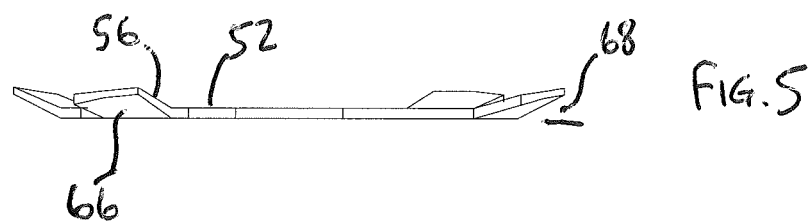

ULTRAVIOLET REACTOR

FIELD OF THE DISCLOSURE

The disclosure relates to an ultraviolet reactor used to irradiate the flow of fluid with ultraviolet light to sterilize or render unharmful microorganisms carried in the fluid.

BACKGROUND OF THE DISCLOSURE

Ultraviolet reactors flow a fluid, such as water, past ultraviolet lamps that irradiate the fluid with ultraviolet light. The ultraviolet light kills or renders harmless a vast majority of potentially harmful microorganisms carried in the fluid.

There is a need for an ultraviolet reactor that is more efficient in exposing microorganisms carried by the fluid to ultraviolet light, resists breaking of the ultraviolet lamps in the event of pressure surges, and in which the lamps can be more easily cleaned or repaired.

SUMMARY OF THE DISCLOSURE

Disclosed is an improved ultraviolet reactor that is more efficient in exposing microorganisms carried by the fluid to ultraviolet light, better resists breaking of the ultraviolet lamps in the event of pressure surges, and in which the lamps can be more easily cleaned or repaired.

An embodiment ultraviolet reactor includes a chamber with a tubular housing and an end wall. The housing defines an interior and extends along an axis between upper and lower ends, the end wall closing the lower end of the housing. An inlet opening is adjacent the lower end of the housing and a discharge opening is adjacent the upper end of the housing, with the housing axis defining a radial direction perpendicular to the axis.

A set of ultraviolet lamps and a set of elongate rods are in the housing, each lamp and each rod extending along a respective axis parallel with the housing axis. A set of baffles are in the housing, the baffles longitudinally spaced apart from one another and attached to the rods. The baffles include a lowermost baffle closest to the end wall, with the rods extending through the other one or more baffles to the lowermost baffle.

Each baffle includes an annular body disposed generally transverse to the longitudinal axis and a plurality of blades extending in the radial direction away from the body, the blades circumferentially spaced apart around the body, each blade having a pitch angle inclined or twisted with respect to the body.

Each baffle body includes a first set of through-holes extending through the baffle body, the lamps extending through and closely received in the first set of holes whereby the baffle body resists radial motion of the lamps passing therethrough.

The blades of each baffle cooperating with one another to urge rotational flow of fluid flowing in the longitudinal direction from the inlet opening towards the upper end of the housing that impinges the blades.

The baffles generate turbulence and impart rotational flow to the fluid as it flows longitudinally from the inlet opening towards the discharge opening. The turbulence and rotational flow enhances exposure of microorganisms to the ultraviolet light emitted by the lamps to improve efficiency of the reactor.

In a preferred embodiment the rods and lamps are attached to a removable head plate closing the top of the fluid chamber. All the lamps can be removed from the chamber at the same time for cleaning, inspection, or repair, or can be inserted into the chamber at the same time.

In further preferred embodiments, the lamps are closely received in holes in the baffles. The baffles and rods cooperate to resist deflection of the lamps in the event of a pressure surge, minimizing the risk of lamp breakage.

Other objects and features will become apparent as the description proceeds, especially when taken in conjunction with the accompanying drawing sheets.

BRIEF DESCRIPTIONS OF THE DRAWINGS

FIG. 4 is a top view of a baffle used in the ultraviolet reactor shown in FIG. 1; and FIG. 5 is a side view of the baffle shown in FIG. 4, the view taken generally along line 5-5 of FIG. 4.

DESCRIPTION OF A PREFERRED EMBODIMENT

Figure 1:
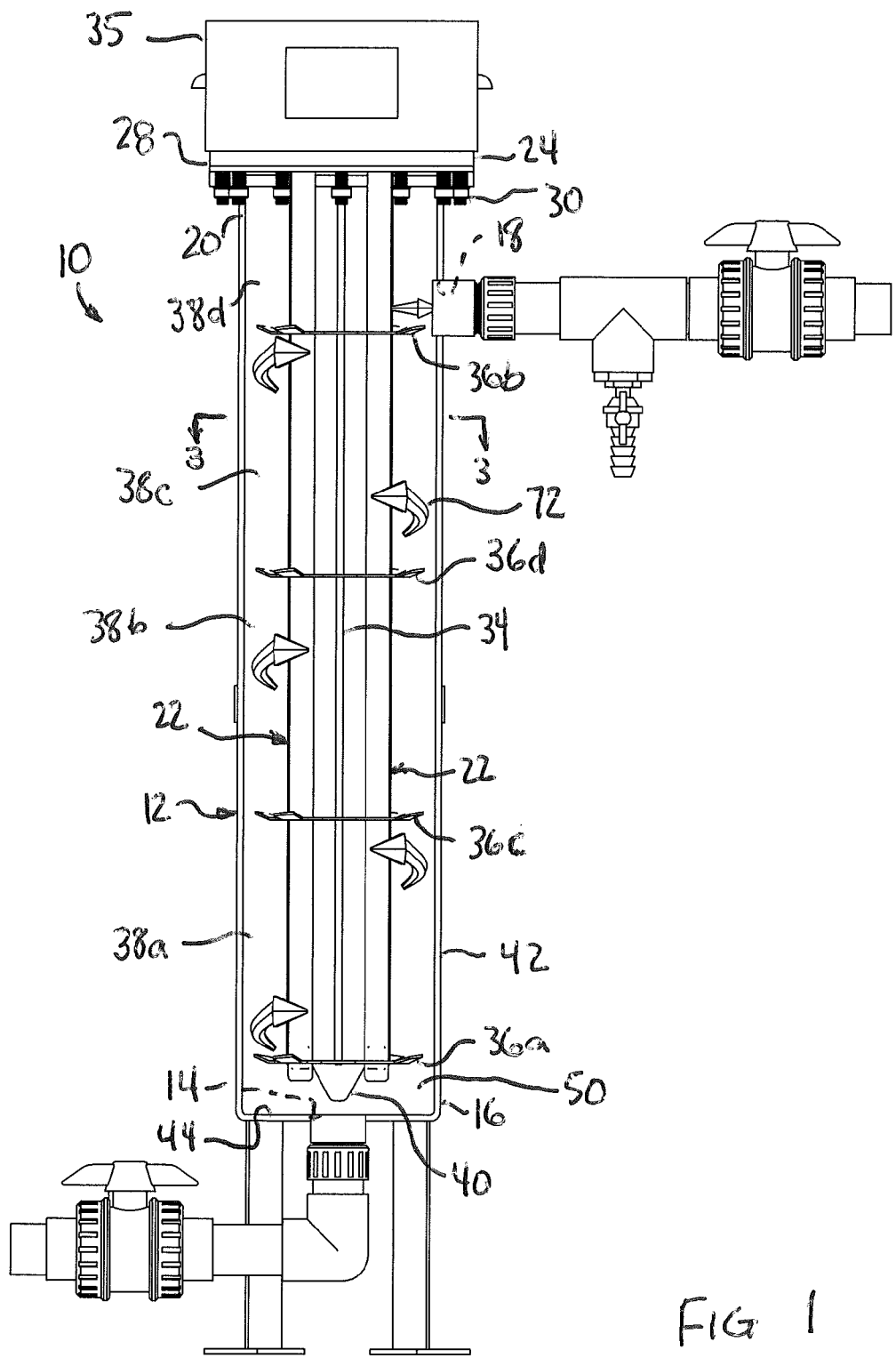
FIG. 1 is a front view of an ultraviolet reactor.
Figure 2:
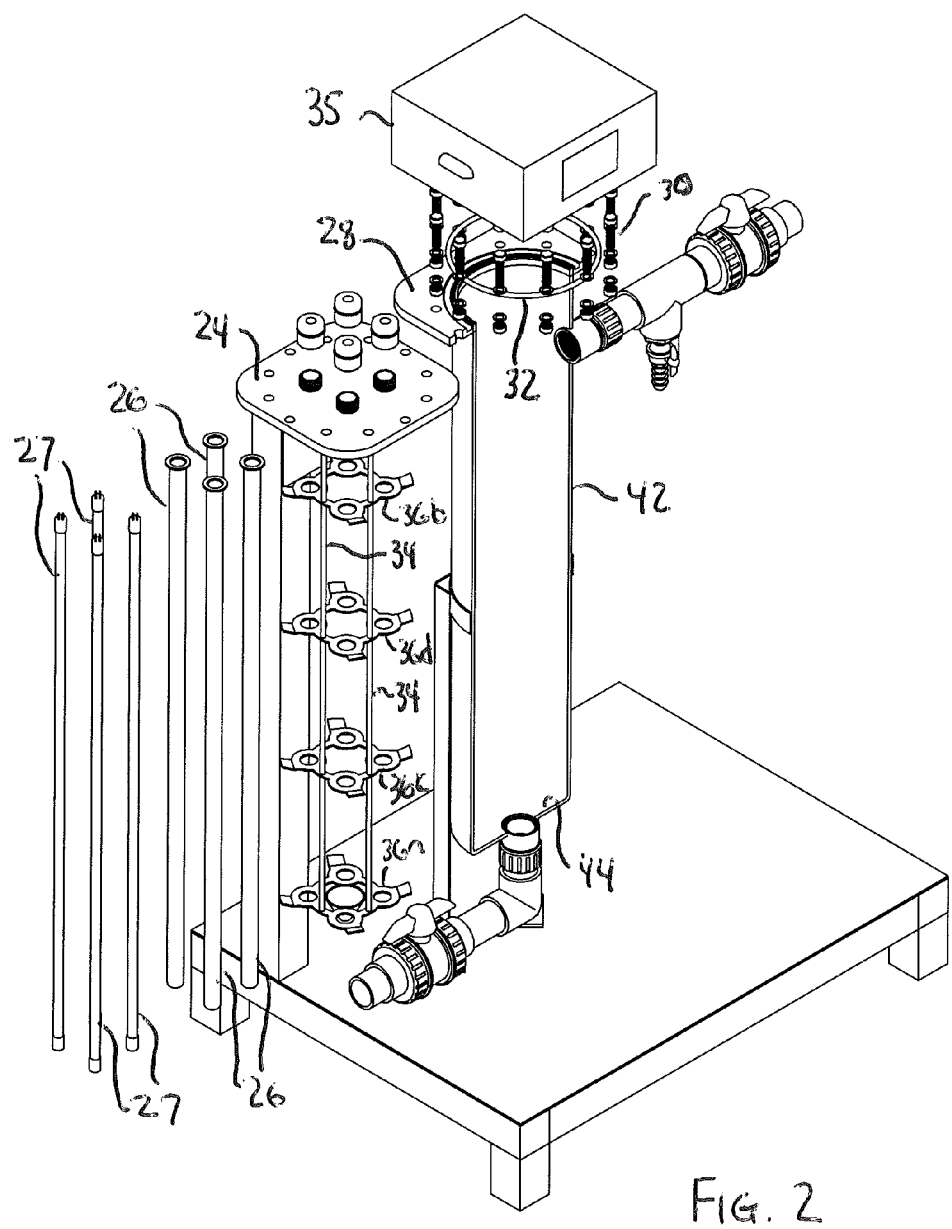
FIG. 2 is an exploded view of the ultraviolet reactor shown in FIG. 1.
Figure 3:
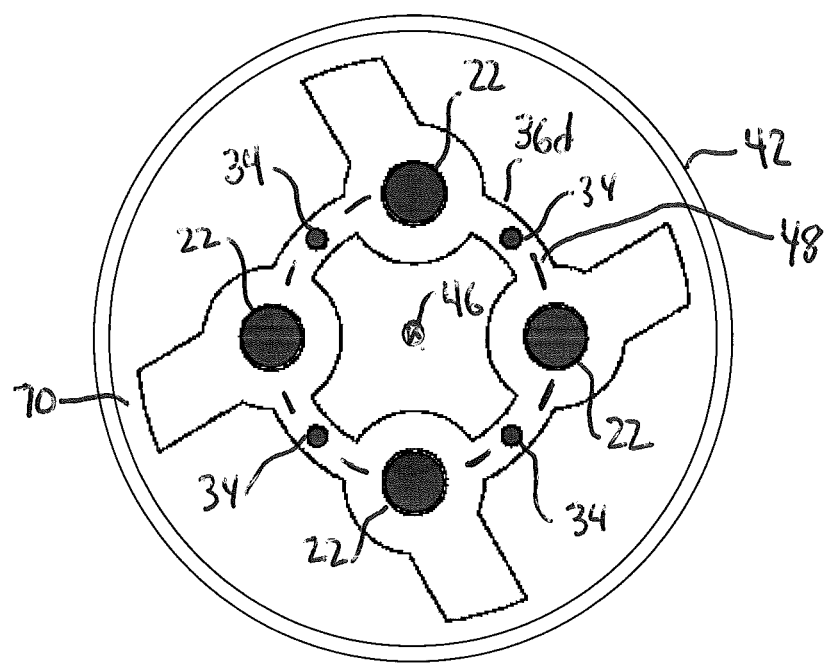
FIG. 3 is a sectional view of the ultraviolet reactor taken along line 3-3 of FIG. 1.

FIGS. 1-3 illustrate an ultraviolet reactor 10. The reactor 10 includes an elongate fluid chamber 12 that receives fluid through an inlet opening 14 at the lower end 16 of the chamber 12 and discharges fluid through a discharge opening 18 adjacent the upper end 20 of the chamber 12. A set of ultraviolet lamps 22 are arranged in the chamber 12, the lamps 22 attached to and extending from a head plate 24 closing the upper end of the chamber 12. The lamps 22 are conventional and include an outer transparent quartz or silica sleeve 26 and an inner filament 27.

The fluid chamber 12 includes an upper flange 28 for mounting the head plate 24, the head plate 24 attached to the flange 28 by gasketed through-fasteners 30. A gasket or O-ring 32 seals the space between the plate 24 and the chamber 12.

A set of elongate stainless steel support rods 34 are also attached to the head plate 24 and extend from the head plate 24 into the fluid chamber 12. The lamps 22 and the rods 34 extend along respective parallel longitudinal axes from the head plate 24 to ends closely spaced from the lower end 16 of the housing 12. The exposed ends of the lamps 22 and the rods 34 are enclosed within a ventilated cover 35 that fits over the head plate 24.

A set of baffles 36 are in the chamber 12, the baffles 36 longitudinally spaced apart from one another and rigidly attached to the rods 34. The set of baffles 36 include a lowermost baffle 36a closest to the chamber's lower end 16, an uppermost baffle 36b closest to the chamber's upper end 20, and intermediate baffles 36c, 36d. The baffles 36 are equally spaced or pitched apart from one another and divide the fluid chamber 12 into respective subchambers or mixing zones 38a, 38b, 38c, 38d located between adjacent pairs of baffles 36 or between the uppermost baffle 36b and the head plate 24. A conical flow diverter 40 is attached to the lower side of the lowermost baffle 36a.

The fluid chamber 12 also includes a tubular housing 42 having a circular cross-section and an end wall 44 closing the lower end 16 of the chamber 12. The housing 42 extends along a central longitudinal axis 46 perpendicular to the drawing sheet as viewed in FIG. 3. The lamps 22 and the rods 34 are symmetrically arranged around the housing axis 46, with the longitudinal axes of the lamps 22 and the rods 34 spaced around a common circle 48 centered on the housing axis 46. The illustrated embodiment has four lamps 22 and four rods 34, the lamps and rods arranged to alternate with one another around the circle 48.

The end wall 44 and the lowermost baffle 36a define an entry chamber or lower subchamber 50 (see FIG. 1) in the chamber 12. The inlet opening 14 is coaxial with the housing axis 46 and extends through the end wall 44 to discharge into the entry chamber 50. The flow diverter 40 extends into the entry chamber 50 and faces the inlet opening 14.

The discharge opening 18 is located in the uppermost mixing zone 38d and extends radially through the tubular wall of the housing 42.

In the illustrated embodiment the baffles 36a, 36b, 36c, 36d are identical to one another and formed from stainless steel. As shown in FIGS. 4 and 5, each baffle 36 includes a flat annular plate or planar body 52 that surrounds a central opening 54, and a set of tabs or blades 56 spaced around the body 52 and extending away from the body 52. A first set of through-holes 58 and a second set of through-holes 60 extend through the thickness of the body 52. The first set of holes 58 are sized and arranged to closely receive the sleeves 26 of the lamps 22. The second set of holes 60 are sized and arranged to closely receive the rods 34, the baffle 36 preferably welded to the rods 34 during assembly of the reactor 10 to fix the longitudinal position of the baffle 34 in the chamber 12. The portions of the body 52 surrounding the holes 58 are radially enlarged for greater strength.

Each blade 56 is essentially a planar member that extends radially away from the body 52 but does not lie in the plane of the body 52. The blade 56 includes opposite generally parallel sides 62, 64 extending away from the body 52 and a lower impingement surface 66 that faces the lower end 16 of the chamber 12. The sides 62, 64 not parallel with the radial direction so that the blade 56 is generally shaped as a non-rectangular parallelogram. The blade 56 is inclined at a pitch angle 68 with respect to the body 52 such that the blade 56 extends towards the upper end 20 of the chamber 12. In the illustrated embodiment the pitch angle 68 is about 25 degrees.

In other embodiments the blades 56 can also be twisted or angularly displaced with respect to the plane of the body 52, similar to the twist or angular displacement of a propeller or turbine blade.

The baffles 46 are sized to define narrow gaps 70 between the blades 56 and the housing 42, see FIG. 3.

Operation of the ultraviolet reactor 10 is discussed next.

Fluid to be irradiated has preferably already passed through one or more upstream filters or fluid treatment devices to remove larger particulates and the like from the fluid prior to irradiation. The fluid flows into the entry chamber 50 through the inlet opening 14 and attempts to flow longitudinally to the discharge opening 18.

The longitudinal flow of fluid impinges against the flow diverter 40, which adds a radial flow that directs the longitudinal fluid flow to impinge against the impingement surfaces 66 of the blades 56 of the lowermost baffle 36a and cause some flow turbulence. The shape and pitch of the blades 56 also urge rotational flow of the fluid in the direction indicated by the arrows 72 (see FIG. 1). The resulting fluid flow through the lowest mixing zone 38a is generally helical, with both longitudinal and rotational flow components about and along the lamps 22 for irradiating the fluid flow.

The fluid flow then successively impinges against the blades 56 of the baffles 36c, 36d, and 36b, the impingement surfaces 66 of the baffle blades 56 again causing turbulence and imparting rotational flow. The blades 56 urge the flow towards the lamps 22 to assure exposure of the fluid to high intensity dosages of radiation from the lamps 22 and thereby maximizing the efficiency of the unit 10 in sterilizing or otherwise rendering harmless microorganisms. The turbulence and the continuous helical fluid flow around the lamps 22 through the mixing zones also combat longitudinal laminar flow along the housing 48 that would reduce the exposure of fluid to the UV radiation. The turbulence and helical flow also combats "shadowing" in which a microorganism is shielded from the lamps 22 by another microorganism or by particulates, thereby reducing the irradiation dosage received by that microorganism.

Any longitudinal flow in the chamber 12 through the sets of baffle openings 56 is flow that is irradiated with high intensity by the lamps 22, ensuring sufficient UV exposure for such flow. The baffle bodies 52, including the enlarged portions surrounding the lamp holes 58 also generate turbulence in any longitudinal flow impinging on them. The rods 34 also assist in generating turbulence and mixing in being in the path of the helically-flowing fluid; the rods 34 in other embodiments may have non-circular cross-sections more resistant to flow around the rods 34 to further enhance rod-generated turbulence if desired.

In the event of a pressure surge or water hammer generated by a sudden fluid shutoff, the baffles 36 and the rods 34 form a support structure that resist radial movement of the lamp sleeves 26, thereby reducing the possibility of cracking the sleeves 24.

For cleanup or repair, the head plate 24 is unfastened from the flange 28, and removing the head plate 24 removes the lamps 22, the rods 34, and the baffles 36 from the housing 12 as a single assembly. This facilitates inspection, repair, and cleaning because all the lamps 22 can be removed from the housing 48 or inserted into the housing 48 at the same time.

While this disclosure has illustrated and described one or more embodiments, it is understood that this is capable of modification, and that the disclosure is not limited to the precise details set forth, but includes such changes and alterations as fall within the purview of the following claims.

What is claimed as the invention is:

1. An ultraviolet reactor for irradiating a flow of fluid with ultraviolet light, the reactor comprising:

a chamber comprising a tubular housing and an end wall, the housing defining an interior and extending along a longitudinal axis between upper and lower ends, the end wall closing the lower end of the housing, an inlet opening adjacent the lower end of the housing and a discharge opening adjacent the upper end the housing, the housing axis defining a radial direction perpendicular to the axis;

a plurality of ultraviolet lamps and a plurality of elongate rods in the housing, each lamp and each rod extending along a respective axis parallel with the housing axis;

a plurality of baffles in the housing, the baffles longitudinally spaced apart from one another and attached to the rods, the baffles comprising a lowermost baffle closest to the end wall, the rods extending through the other one or more baffles to the lowermost baffle;

each baffle comprising an annular body disposed generally transverse to the longitudinal axis and a plurality of blades extending in the radial direction away from the body, the blades circumferentially spaced apart around the body, each blade inclined or twisted with respect to the body;

each baffle body comprising a first set of through-holes extending through the baffle body, the lamps extending through and closely received in the first set of holes whereby the baffle body resists radial motion of the lamps passing therethrough, and the blades of each baffle cooperating with one another to urge rotational flow of fluid flowing in the longitudinal direction from the inlet opening towards the upper end of the housing that impinges the blades.

2. The ultraviolet reactor of claim 1 wherein each baffle body defines a plane transverse to the longitudinal axis and the blades of the baffle are inclined at an angle of about 25 degrees with respect to the plane.

3. The ultraviolet reactor of claim 1 wherein the plurality of baffles comprises an uppermost baffle closest to the upper end of the housing, the discharge opening between the uppermost baffle and the upper end of the housing.

4. The ultraviolet reactor of claim 1 wherein the inlet opening extends through the end wall, and the reactor further comprises a conical flow diverter attached to the lowermost baffle and opposite the inlet opening.

5. The ultraviolet reactor of claim 4 wherein the conical flow diverter blocks the opening surrounded by the lowermost baffle.

6. The ultraviolet reactor of claim 1 wherein the axes of the rods and lamps are arranged along a common circle.

7. The ultraviolet reactor of claim 6 wherein the rods and lamps alternate with one another around the common circle.

8. The ultraviolet reactor of claim 1 comprising a removable end plate closing the upper end of the housing, the rods and lamps fixed to the end plate for conjoint movement with the end plate when removing the end plate from the housing.

9. The ultraviolet reactor of claim 1 wherein the baffles are longitudinally spaced at an equal pitch.

10. The ultraviolet reactor of claim 1 wherein the ultraviolet lamps are arranged around the longitudinal axis of the housing, the lamps disposed closer to the axis than to the housing.

11. The ultraviolet reactor of claim 1 wherein there is clearance between the blades of each baffle and the housing.

12. The ultraviolet reactor of claim 1 wherein the blades of each baffle extend towards the upper end of the housing as they extend away from the baffle body.

13. The ultraviolet reactor of claim 1 wherein the body of each baffle includes a second set of holes, the rods extending through the second set of holes.

14. The ultraviolet reactor of claim 1 wherein the baffles are welded to the rods.

\* \* \* \* \*